US00PP21729P2

(12) United States Plant Patent
Gass

(10) Patent No.: US PP21,729 P2
(45) Date of Patent: Feb. 22, 2011

(54) *HESPERALOE* PLANT NAMED 'PERPA'
(50) Latin Name: *Hesperaloe parviflora*
Varietal Denomination: Perpa

(76) Inventor: Ronald Gass, P.O. Box 2500, Litchfield Park, AZ (US) 85340

( * ) Notice: Subject to any disclaimer, the term of this patent is extended or adjusted under 35 U.S.C. 154(b) by 0 days.

(21) Appl. No.: 12/583,681

(22) Filed: Aug. 25, 2009

(51) Int. Cl.
*A01H 5/00* (2006.01)

(52) U.S. Cl. ..... Plt./263.1

(58) Field of Classification Search ..... Plt./263.1

See application file for complete search history.

*Primary Examiner*—Wendy C. Haas
(74) *Attorney, Agent, or Firm*—C. A. Whealy

(57) ABSTRACT

A new and distinct cultivar of *Hesperaloe* plant named 'Perpa', characterized by its upright plant habit; vigorous growth habit; elongated lanceolate green-colored leaves; campanulate red-colored flowers with flared apices; and good garden performance.

1 Drawing Sheet

Botanical designation: *Hesperaloe parviflora.*
Cultivar denomination: 'PERPA'.

BACKGROUND OF THE INVENTION

The present invention relates to a new and distinct cultivar of *Hesperaloe* plant, botanically known as *Hesperaloe parviflora* and hereinafter referred to by the name 'Perpa'.

The new *Hesperaloe* plant is a product of a planned breeding program conducted by the Inventor in Litchfield Park, Ariz. The objective of the breeding program is to develop new *Hesperaloe* plants with unique flower coloration.

The new *Hesperaloe* plant originated from a self-pollination in 2002 of an unnamed selection of *Hesperaloe parviflora,* not patented. The new *Hesperaloe* plant was discovered and selected by the Inventor in 2006 as a single flowering plant within the progeny of the stated self-pollination in a controlled environment in Litchfield Park, Ariz.

Asexual reproduction of the new *Hesperaloe* plant by tissue culture in a controlled greenhouse environment since 2006 has shown that the unique features of this new *Hesperaloe* plant are stable and reproduced true to type in successive generations of asexual reproduction.

SUMMARY OF THE INVENTION

Plants of the new *Hesperaloe* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Perpa'. These characteristics in combination distinguish 'Perpa' as a new and distinct cultivar of *Hesperaloe:*

1. Upright plant habit.
2. Vigorous growth habit.
3. Elongated lanceolate green-colored leaves.
4. Campanulate red-colored flowers with flared apices.
5. Good garden performance.

Plants of the new *Hesperaloe* can be compared to plants of the parent selection. Plants of the new *Hesperaloe* differ from plants of the parent selection in the following characteristics:

1. Flowers of plants of the new *Hesperaloe* are campanulate in shape with flared apices whereas flowers of plants of the parent selection are tubular in shape.
2. Flowers of plants of the new *Hesperaloe* are red in color whereas flowers of plants of the parent selection are light coral pink in color.

Plants of the new *Hesperaloe* can be compared to plants of the *Hesperaloe parviflora* 'Yellow', not patented. Plants of the new *Hesperaloe* differ from plants of 'Yellow' in the following characteristics:

1. Flowers of plants of the new *Hesperaloe* are campanulate in shape with flared apices whereas flowers of plants of 'Yellow' are tubular in shape.
2. Flowers of plants of the new *Hesperaloe* are red in color whereas flowers of plants of 'Yellow' are creamy yellow in color.

BRIEF DESCRIPTION OF THE PHOTOGRAPHS

The accompanying colored photographs illustrate the overall appearance of the new *Hesperaloe* plant, showing the colors as true as it is reasonably possible to obtain in colored reproductions of this type. Colors in the photographs may differ slightly from the color values cited in the detailed botanical description which accurately describe the colors of the new *Hesperaloe* plant.

The photograph at the top of the sheet is a side perspective view of a typical plant of 'Perpa' grown in a container.

The photograph at the bottom of the sheet is a close-up view of a typical inflorescence of 'Perpa'.

DETAILED BOTANICAL DESCRIPTION

The aforementioned photographs and following observations, measurements and values describe plants of the new *Hesperaloe* grown in 6-cm containers in Phoenix, Ariz. during the summer in an outdoor nursery and under conditions which closely approximate commercial production. Plants were two years old when the photographs and the description were taken. In the description, color references are made to The Royal Horticultural Society Colour Chart, 2007 Edition, except where general terms of ordinary dictionary significance are used.

Botanical classification:

*Hesperaloe parviflora.*—'Perpa'.

Parentage: Self-pollination of an unnamed selection of *Hesperaloe parviflora,* not patented.

Propagation:

*Type.*—By tissue culture.

Plant description:

*Plant form and growth habit.*—Perennial shrub; upright plant habit; vigorous growth habit; leaves arranged in a basal rosette with a central flower stalk.

*Plant height, from soil level to top of inflorescence.*—About 60 cm.

*Plant height, from soil level to top of foliar plane.*—About 42 cm.

*Plant diameter* (*area of spread*).—About 32 cm.

Stem description:

*Internode length.*—About 3 mm.

*Texture.*—Smooth, glabrous.

*Color.*—Close to 155A.

Foliage description:

*Arrangement.*—In a basal rosette, whorled; simple; sessile.

*Length.*—About 39.5 cm.

*Width.*—About 6 mm; at the base, about 2 cm.

*Shape.*—Elongated lanceolate.

*Apex.*—Acuminate.

*Base.*—Truncate; clasping the stem.

*Margin.*—Entire; filiferous.

*Texture, upper and lower surfaces.*—Smooth, glabrous; rigid, tough; longitudinally ridged.

*Venation pattern.*—Parallel.

*Color.*—Developing leaves, upper and lower surfaces: Close to 138A. Fully expanded leaves, upper surface: Close to 138B; venation, close to 138A. Fully expanded leaves, lower surface: Close to 138A; towards the base, close to 145D; venation, close to 138A.

Flower description:

*Flower appearance/arrangement.*—Single campanulate flowers arranged in upright racemes; flowers with flared petal apexes; freely flowering habit with usually about 68 flowers per inflorescence; flowers initially face upright and then face outwardly with development.

*Natural flowering season.*—Continuous flowering from March to late summer in Arizona.

*Flower longevity.*—Individual flowers last about five days on the plant; flowers not persistent.

*Fragrance.*—None detected.

*Inflorescence height.*—About 21.5 cm.

*Inflorescence diameter.*—About 5.8 cm.

*Flower length.*—About 2 cm.

*Flower diameter.*—About 1.8 cm.

*Flower bud.*—Length: About 1.5 cm. Diameter: About 5 mm. Shape: Oblong. Color: Close to 54A.

*Flower segments.*—Quantity per flower: Six segments fused towards the base; apices flared. Length: About 1.7 cm to 1.8 cm. Width: About 6 mm. Shape: Elliptical. Apex: Acute. Margin: Entire. Texture, upper and lower surfaces: Smooth, glabrous. Color: When opening, upper surface: Close to 51C. When opening, lower surface: Close to 54A. Fully opened, upper surface: Close to 53D; color becoming closer to 51B with development. Fully opened, lower surface: Close to 53D; color does not fade with development.

*Peduncles.*—Length: About 34 cm. Diameter: About 4.5 mm. Strength: Strong. Aspect: Upright. Texture: Smooth, glabrous. Color: Close to 186B.

*Pedicels.*—Length: About 1.2 cm. Diameter: About 1 mm. Strength: Strong. Aspect: About 30° to 40° from peduncle axis. Texture: Smooth, glabrous. Color: Close to 53D.

*Reproductive organs.*—Androecium: Quantity per flower: About six. Filament length: About 1.1 cm. Filament color: Close to 55C to 55D. Anther shape: Oval. Anther length: About 2.5 mm. Anther color: Close to 18A. Amount of pollen: Moderate. Pollen color: Close to 6A. Gynoecium: Quantity per flower: One. Pistil length: About 2 cm. Style length: About 1.4 cm. Style color: Close to 51D. Stigma appearance: Capitate. Stigma color: Close to NN155D. Ovary color: Close to 155B.

*Fruits/seeds.*—Fruit and seed development has not been observed.

Garden performance: Plants of the new *Hesperaloe* have been observed to have good garden performance and to tolerate rain, wind and temperatures ranging from about −20° C. to about 45° C.

Pathogen/pest resistance: Plants of the new *Hesperaloe* have not been observed to be resistant to pathogens and pests common to *Hesperaloe.*

It is claimed:

1. A new and distinct *Hesperaloe* plant named 'Perpa' as illustrated and described.

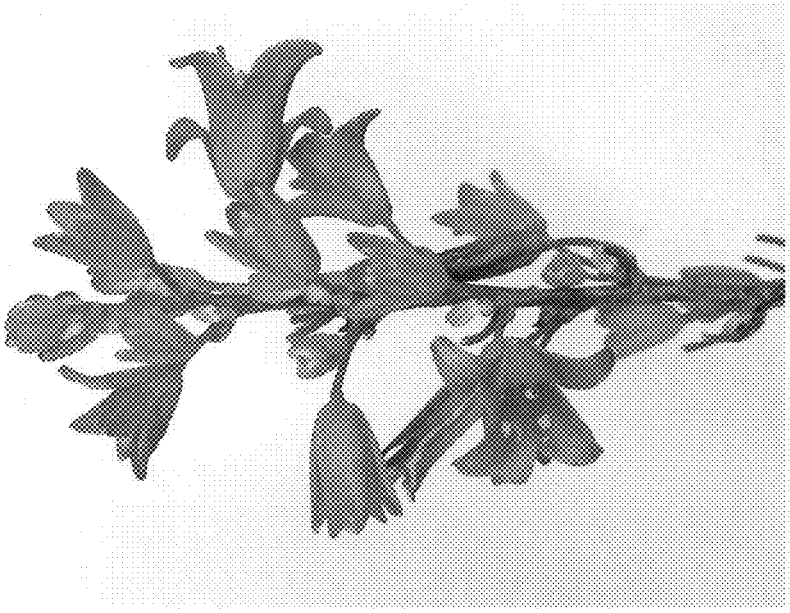
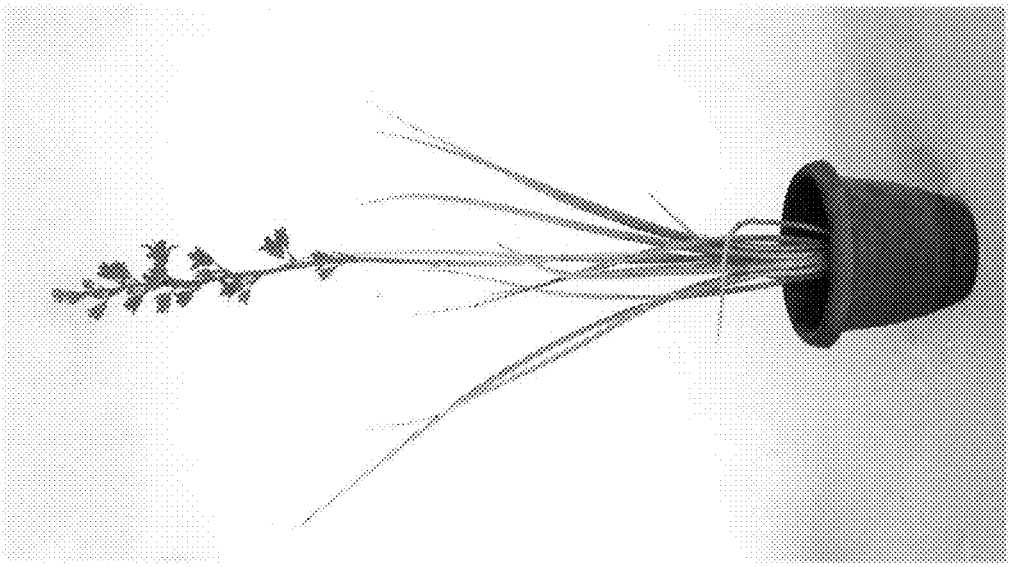

* * * * *